(12) United States Patent
Smirnov

(10) Patent No.: US 7,879,560 B2
(45) Date of Patent: Feb. 1, 2011

(54) NANOTUBE STRUCTURES HAVING A SURFACTANT BILAYER INNER WALL COATING

(75) Inventor: Alex I. Smirnov, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 239 days.

(21) Appl. No.: 12/330,010

(22) Filed: Dec. 8, 2008

(65) Prior Publication Data

US 2010/0331202 A1 Dec. 30, 2010

Related U.S. Application Data

(62) Division of application No. 10/865,318, filed on Jun. 10, 2004, now Pat. No. 7,521,225.

(60) Provisional application No. 60/478,200, filed on Jun. 13, 2003.

(51) Int. Cl.
*G01N 33/53* (2006.01)
(52) U.S. Cl. .................... 435/7.1; 435/6; 436/523; 436/532; 436/71; 427/358; 427/384
(58) Field of Classification Search .................. None
See application file for complete search history.

(56) References Cited

U.S. PATENT DOCUMENTS

| | | | |
|---|---|---|---|
| 6,180,114 B1 | 1/2001 | Yager et al. | |
| 2002/0118027 A1 | 8/2002 | Routkevitch et al. | |
| 2003/0102263 A1 | 6/2003 | Lopez et al. | |
| 2004/0173506 A1 | 9/2004 | Doktycz et al. | |
| 2006/0014013 A1 | 1/2006 | Saavedra et al. | |

OTHER PUBLICATIONS

Hennesthal et al.; "Pore-Spanning Lipid Bilayers Visualized by Scanning Force Microscopy," *J. Am. Chem. Soc.*, 2000, 122, pp. 8085-8086.
Lee et al.; "Antibody-Based Bio-Nanotube Membranes for Enantiomeric Drug Separations," *Science*, 2002, vol. 296, pp. 2198-2200.
Martin et al.; "The Emerging Field of Nanotube Biotechnology," *Nature Reviews*, 2003, vol. 2, pp. 29-37.
Smirnov et al.; "Substrate-Supported Lipid Nanotube Arrays," pp. 1-2, 2003.
Tonucci et al.; "Nanochannel Array Glass," *Science*, 1992, vol. 258, 783-785.
University of Florida, "Biosensors," www.chem.ufl.edu/~crmartin/biosensor.html, dated Jun. 9, 2003, 1 page.
University of Florida, "Nanotubes and Nanotube Membranes," www.chem.ufl.edu/~crmartin/nnmembrane.html, dated Jun. 9, 2003, 1 page.
University of Florida, "Recently Really Cool Articles," www.chem.ufl.edu/~crmartin/rrccarticles.com, dated Jun. 9, 2003, 1 page.
International Search Report for PCT/US04/18651; Date of Mailing Dec. 21, 2004.

*Primary Examiner*—Nelson Yang
(74) *Attorney, Agent, or Firm*—Myers Bigel Sibley & Sajovec, P.A.

(57) ABSTRACT

Nanotubes and nanotube array structures comprise (a) a nanotube having an inner wall portion; and (b) a bilayer coating formed on the inner wall portions, with the bilayer coating comprised of surfactants. A secondary compound such as a protein, peptide or nucleic acid may be associated with the bilayer coating. The structures are useful for, among other things, affinity purification, catalysis, and as biochips.

15 Claims, 8 Drawing Sheets

(Prior Art Planar Lipid Array)

(Lipid Nanotube Array)

NANOTUBE STRUCTURES HAVING A SURFACTANT BILAYER INNER WALL COATING

RELATED APPLICATIONS

This application is a divisional of and claims priority to U.S. patent application Ser. No. 10/865,318, filed Jun. 10, 2004, now U.S. Pat. No. 7,521,225 and claims the benefit of U.S. Provisional Application Ser. No. 60/478,200, filed Jun. 13, 2003, the disclosure of each of which is incorporated by reference herein in its entirety.

GOVERNMENT FUNDING

This invention was made with Government support under DOE Contract DE-FG02-02ER15354. the Government has certain rights to this invention.

FIELD OF THE INVENTION

The present invention generally relates to nanotubes and nanotube arrays, membrane biochips, and protein biochips along with methods of making the same.

BACKGROUND OF THE INVENTION

Substrate-supported phospholipid bilayers are of interest for many reasons. Firstly, these bilayers represent a convenient and versatile model of cellular membranes. Starting with the studies of McConnell and coworkers,[1,2] it is now well documented that phospholipid vesicles fuse spontaneously into planar membranes when incubated on treated surfaces.[3,4] In such planar assemblies the lipids are mobile as in vesicles[4] and are suitable for incorporation of transmembrane proteins.[2] Secondly, many inorganic substrates can be functionalized by self-assembling lipid bilayers on the surfaces.[3] This substrate biofunctionalization is considered by many authors as one of the most attractive ways for building hybrid nanoscale devices and combinatorial assays to screen protein and phospholipid libraries for specific membrane-protein interactions.[3,4] Recently, Boxer and coworkers described spatially addressable libraries of chemically distinct phospholipids that can be used for such a screening and also for studying the mechanisms of such important intracellular processes as protein trafficking and cell activation.[4,5] Another potential use of the phospholipid arrays is for pattering of membrane proteins that would not require covalent attachment of proteins to the surface.

While several different approaches for building substrate-supported membranes are described in the literature,[3,4,6] essentially all of them are based on a planar design in which phospholipids are patterned/deposited on mostly essentially flat surfaces (see FIG. 1). Planar bilayers can be assembled by covalently attaching the inner monolayer to the substrate. These substrate-supported bilayers are very stable but lack some phospholipid mobility that can be achieved when the entire bilayer is suspended from the substrate on an ultrathin 5-15 Å water and/or polymer layer. The latter planar bilayer exhibits a greater resemblance with cellular membranes.[4] In addition, suspended bilayers are more suitable for incorporation of membrane peptides and proteins because there is less steric congestion on the substrate side than for covalently-attached bilayers. Spanning planar bilayers over the outside surface of anodically etched porous alumina might be helpful for decreasing the congestion for those regions of the bilayer that lay above the pores.[6]

Although planar phospholipid membranes are ideally suited for surface spectroscopy and imaging,[4,5,7] this technology has some limitations for building robust arrays of biosensors. Particularly, the planar lipid assemblies and protein-on-a-chip devices are very fragile because the entire surface of the chip is exposed to the environment. Even any minor mechanical perturbation or contamination of the surface such as, e.g., an accidental touching or scratching, would be of a catastrophic consequence to the fragile phospholipid assembly. Also, in order to maintain the phospholipid order the surface of such an array should be kept hydrated and special care should be taken to keep this type of biochip from drying. In addition, the maximum number of lipid molecules and membrane proteins that could be deposited on such a chip is limited by the area of the planar supporting surface minus the total area of barriers.

SUMMARY OF THE INVENTION

A first aspect of the present invention is an article of manufacture comprising: (a) a nanotube having an inner wall portion; and (b) a bilayer coating formed on the inner wall portions, with the bilayer coating comprised of surfactants. In a particular embodiment the article comprises: (a) a nanotube having an inner wall portion, said nanotube having (i) an inner diameter between 10 nanometers and 500 nanometers and (ii) a length from two to one thousand times said diameter; and (b) a bilayer coating formed on said inner wall portion, with said bilayer coating comprised of (i) from 10, 20 or 30 to 70, 80 or 90 percent by weight surfactants and (ii) from 10, 20 or 30 to 70, 80 or 90 percent by weight of water.

A second aspect of the present invention is a nanotube array comprising: (a) a substrate having a plurality of nanotubes formed therein, each of the nanotubes having an inner wall portion; and (b) a bilayer coating formed on each of the inner wall portions; the bilayer coating comprised of surfactants. The bilayer coating can be attached to the inner wall portion or suspended in close proximity to the inner wall without actual attachment (e.g., without covalent bond). Several bilayer coatings inside a single nanotube can be formed if desired.

A third aspect of the present invention is a patterned nanotube array comprising: (a) a substrate having a plurality of nanotubes formed in separate and discrete regions therein, each of the nanotubes having an inner wall portion; (b) a bilayer coating formed on each of the inner wall portions; the bilayer coating comprised of surfactants; and (c) a secondary compound associated with the bilayer coating, wherein the secondary compound in each one of the separate and discrete regions differs from the secondary compound in each other of the separate and discrete regions.

In some embodiments of the foregoing, the surfactant comprises a phospholipid.

In some embodiments of the foregoing, an additional secondary compound such as a protein or a peptide is associated with the bilayer coating.

The foregoing and other objects and aspects of the present invention are explained in greater detail in the drawings herein and the specification set forth below.

DETAILED DESCRIPTION OF THE PREFERRED EMBODIMENTS

Figure 1:
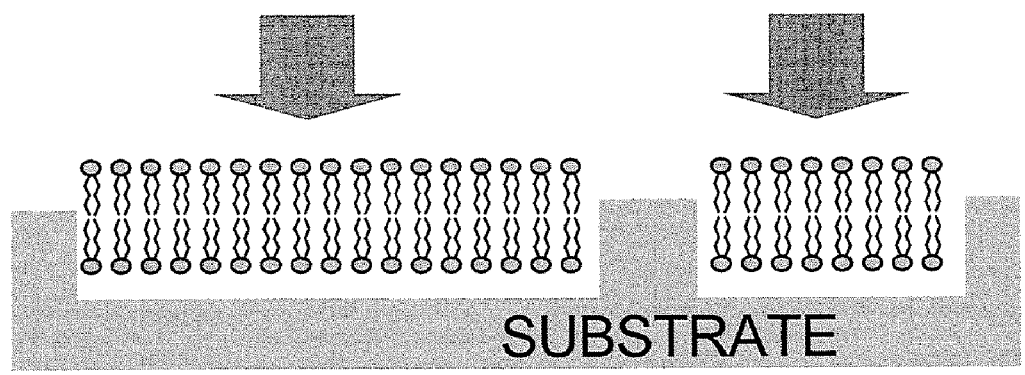
FIG. 1 illustrates a planar substrate-supported bilayer of the prior art.

Nanotubes and nanotube arrays embedded in a substrate used to carry out the present invention are known and may be produced in accordance with known techniques. In one embodiment the nanotubes are provided as an array of a plurality of nanotubes formed in a substrate (or assembled together into a substrate), which array generally comprises a plurality of parallel aligned nanotubes (e.g., substantially mutually aligned nanotubes with a direction or axial dimension substantially perpendicular to the substrate surface). The nanotubes may be formed of any suitable material including but not limited to carbon, glass, silicon, metals and metal oxides such as aluminum oxide, polymers such as polycarbonate, or any other suitable other nonconductive, conductive or semiconductive material. In general the nanotubes have an inner diameter of from about 10, 20, or 50 nanometers up to 200, 500 or even 1000 nanometers. The length of the nanotubes is not critical, but in some embodiments will be from two, three, five, ten, one hundred or even one thousand times the diameter of the nanotube, or more. The nanotubes may be open at both end portions thereof, or closed at one (or if desired both) end portions by either manufacturing or sealing after formation thereof in the manner described herein. The nanotubes need not be perfectly cylindrical in cross-section or inner diameter, but may be in any suitable shape, including but not limited to oval, square, hexagonal (including generally or substantially hexagonal with rounded corners or "honeycombed"), irregular (with diameter representing average diameter), including nanotubes that branch out into smaller nanotubes, etc.

Surfactants for carrying out the present invention are, in general, amphiphilic compounds comprising (i) a polar or hydrophilic group coupled to (ii) a nonpolar, lipophilic or hydrophobic group. A single surfactant may be used, or a combination of surfactants may be used. Numerous surfactants are known to those skilled in the art. See, e.g., McCutcheon's Volume 1: Emulsifiers & Detergents (1995 North American Edition) (MC Publishing Co., 175 Rock Road, Glen Rock, N.J. 07452). Examples of the major surfactant types that can be used to carry out the present invention include the: alcohols, alkanolamides, alkanolamines, alkylaryl sulfonates, alkylaryl sulfonic acids, alkylbenzenes, amine acetates, amine oxides, amines, sulfonated amines and amides, betaine derivatives, block polymers, carboxylated alcohol or alkylphenol ethoxylates, carboxylic acids and fatty acids, a diphenyl sulfonate derivatives, ethoxylated alcohols, ethoxylated alkylphenols, ethoxylated amines and/or amides, ethoxylated fatty acids, ethoxylated fatty esters and oils, fatty esters, fluorocarbon-based surfactants, glycerol esters, glycol esters, hetocyclic-type products, imidazolines and imidazoline derivatives, isethionates, lanolin-based derivatives, lecithin and lecithin derivatives, lignin and lignin derivatives, maleic or succinic anhydrides, methyl esters, monoglycerides and derivatives, olefin sulfonates, phosphate esters, phosphorous organic derivatives, polyethylene glycols, polymeric (polysaccharides, acrylic acid, and acrylamide) surfactants, propoxylated and ethoxylated fatty acids alcohols or alkyl phenols, protein-based surfactants, quaternary surfactants, sarcosine derivatives, silicone-based surfactants, soaps, sorbitan derivatives, sucrose and glucose esters and derivatives, sulfates and sulfonates of oils and fatty acids, sulfates and sulfonates ethoxylated alkylphenols, sulfates of alcohols, sulfates of ethoxylated alcohols, sulfates of fatty esters, sulfonates of benzene, cumene, toluene and xylene, sulfonates of condensed naphthalenes, sulfonates of dodecyl and tridecylbenzenes, sulfonates of naphthalene and alkyl naphthalene, sulfonates of petroleum, sulfosuccinamates, sulfosuccinates and derivatives, taurates, thio and mercapto derivatives, tridecyl and dodecyl benzene sulfonic acids, etc. In one embodiment, phospholipid surfactants are preferred.

Secondary compounds utilized to carry out the present invention may, for example, be proteins or peptides, nucleic acids (e.g., DNA or RNA), sugars, carbohydrates, lipids, small organic compounds, etc. The secondary compound may be associated with (e.g., coupled to, embedded in, bound to, etc.) the bilayer by any suitable technique, such as by selecting secondary compounds that contain lipophilic regions that embed in and associate with the bilayer (e.g., membrane proteins), coupling compounds to a lipophilic compound that in turn associates with the bilayer, encapsulating the secondary compound in a lipophilic vesicle such as a liposome, covalently attaching the secondary compound to some of the molecules forming the bilayer, etc. The secondary compound may be included in the bilayer composition in any suitable amount, typically from 1, 2 or 3 percent by weight up to 20, 30 or 40 percent by weight.

In general, a method of depositing a surfactant bilayer on the interior wall of a nanotube, comprising the steps of: (a) providing a nanotube or nanotube array having an open end portion an inner wall portion; (b) providing a surfactant solution, typically an aqueous solution, and typically containing surfactant vesicle; and (c) contacting a solution of a different polarity (for example, aqueous solution, alcohol solution) to the nanotube open end portion for a time sufficient to form a bilayer of the surfactant on the inner wall portion of the nanotube (e.g., the nanotubes within a nanotube array). In one preferred embodiment, the contacting step is carried out at temperature above the main phase transition temperature of the surfactant, or to keep the bilayer at a temperature within the fluid bilayer phase. For example, for DMPC this temperature is about 23° C., while for DPPC this temperature is about 40.5° C. Phase properties of phospholipids are known and described in, for example, D. Marsh, CRC Handbook of Lipid Bilayers (CRC Press 1990).

In one embodiment, a dry AAO substrate is contacted to a liquid aqueous dispersion of phospholipids at a temperature above the phase transition (e.g., in a fluid bilayer phase) from one side. Within one minute or so the pores of the nanotubes were filled in. This configuration is preferably maintained for about five minutes which appears to result in some water evaporation and permit more lipids to get inside the nanotubes.

Satisfactory coating of nanotube walls is also achieved by assisting with centrifugation. In this technique a dry AAO substrate is placed flat on a dry porous support (e.g., a cellulose membrane of a microconcentrator), aqueous phospholipid dispersion is placed on top, and the centrifuge switched on thus pushing phospholipids through the nanotubes (thus utilizing increased gravity to push the surfactants into the nanotubes). A similar effect is achieved by using hydrostatic pressure from one side. Again the membrane is preferably in a fluid bilayer phase. The first method is simpler but, for smaller nanotube sizes and/or for longer chain surfactants or phospholipids, centrifuge- or pressure-assisted deposition may be preferred.

A uniform satisfactory coating can be achieved by preparing small unilamellar vesicles (SUV), also called liposomes, using methods described, for example, by Barenholtz et al. (Biochemistry, 16, 2806-2810 (1977) or by extrusion using, for example, Lipofast extruder from Avestin. The diameter of these SUV structures is typically 20, 30, 50, or 100 nm. Liposomes of the larger diameter such as 150, 200, and 400 nm can be also used. These liposomes are dispersed and are free flowing in an aqueous buffer. The buffer solution is then forced using hydraulic pressure through the nanoporous substrate containing pores open with both ends. Upon flowing through the substrate the lipids become attached to the surface forming a nanotubular structure by a self-assembly mechanism.

As noted above, a secondary compound may be associated with the bilayer coating, either by including the secondary compound in the surfactant solution during the contacting step, or adding the secondary compound to the bilayer after it is formed. Where patterning of the secondary compound within the bilayer is desired (e.g., as in a protein or nucleic acid chip), such patterning may be achieved by any suitable means, such as microstamping the substrate with the secondary compound, "writing" the secondary compound onto the substrate with a micropipette, using robotic printing with a pin (i.e., by dipping a pin into a container with a second compound and then transferring this compound from the pin surface to the substrate during mechanical contact), polymer lift-off techniques such as described in U.S. Pat. No. 5,057, 399, etc. (The disclosures of all United States patents cited herein are to be incorporated herein by reference).

An important feature of the instant process is the formation of the bilayer(s) inside the nanotube by self assembly, which self assembly can be assisted by capillary, electrostatic, gravitational or other forces.

Another important feature of the instant process is the self assembly of the bilayered structures, which are non necessarily nanotubular in shape, can be carried out outside the nanopores, with consequent filling of the nanopores assisted by capillary, electrostatic, gravitational or other forces.

If the self-assembly of the bilayered structures is carried out outside the nanopores, then the phase state of the bilayered structure should be appropriate to adapt to nanotubular configuration inside the nanopore. The phase state of the bilayered structure can be manipulated by temperature and pressure.

In some embodiments of the foregoing the multilamellar liposomes formed from a phospholipid should be in a fluid bilayer phase in order to fill the nanopores in an efficient way. The same nanopores cannot be filled if the same liposomes are frozen. The filling of the nanopores may be less efficient if the phospholipid bilayer are in other than fluid bilayer phase. One example of such a phase is a liquid crystalline phase.

One advantage of the nanotube structures of the present invention is the stability of their surfactant bilayer inner wall coating. For example, the nanotubes may be provided in a hydrated (aqueous) form or dried form. When provided in aqueous form the surfactant coating retains its bilayer structure. When provided in dried nonaqueous faun the surfactant coating does not retain substantial bilayer structure, but the surfactants self-assemble inside the nanopores or nanotubes into a bilayer structure when they are rehydrated. When provided in aqueous or nonaqueous form, the nanotubes preferably have a long shelf life (for example, exhibit a static order parameter of at least 0.6, 0.7, 0.8 or 0.9 when stored under refrigerated conditions (e.g., at a temperature of 4° C.) for 1, 2, or even 4 or more months. Lower temperatures such as −20 or −80° C. increase the shelf life. In many cases stability is determined by shelf-life of the molecules utilized for the surfactant bilayer coating. Note that many planar suspended bilayer structures are not stable and cannot be stored in dry form.

In some embodiments, a second advantage of the present invention is that a much larger surface area for bilayer formation is achieved as compared to the planar area of the substrate surface. In some embodiments of the foregoing the surface area coated with bilayer in the substrate exceeds the planar surface area of the substrate by a factor of ten, one hundred or even one thousand or more.

A further advantage of some embodiments of the present invention is that, by placing the bilayer coating inside the substrate nanopores or nanotubes, the bilayer coating is protected from surface contaminants which are larger than the diameter of the nanotubes (while allowing smaller molecules to enter and leave the nanotubes).

A further advantage of some embodiments of the present invention is that, while bilayered structures inside the nanotubes substantially retain the physical, chemical, and biological properties of bilayered assemblies formed in the absence of support, each particular structure is confined to a particular nanotube in a substrate, thus allowing spatial encoding that is not possible for unsupported structures formed from the same molecules.

Nanotubes and nanotube arrays of the present invention are useful, among other things, as biosensors or microarrays (e.g., "protein on a chip" microarrays) for diagnostic or research purposes, where the binding of other compounds to the secondary compounds can be determined, in accordance with known techniques. Nanotube arrays of the present invention can be used as enzyme beds for catalytic reactions, as filter and chromatography substrates, etc., in some embodiments with or without the inclusion of the secondary compound in the bilayer.

Purification. Thus one particular application of the invention is a method of binding a first member of a specific binding pair, comprising: providing an article of manufacture (including nanotube arrays and nanotube beds) as describe herein, said article further comprising a secondary compound associated with said bilayer coating, wherein said secondary compound is a second member of said specific binding pair; and then contacting a composition containing said first member of said specific binding pair to said article of manufacture so that first member of said specific binding pair binds to said second member of said specific binding pair and is thereby bound to bilayer coating formed on said inner wall portion of said nanotube. The method may further comprise the steps of: separating said composition from said article of manufacture; and then releasing said first member of said specific binding pair from said second member of said specific binding pair. In some embodiments the first member of said specific binding pair is a protein or peptide or nucleic acid; in some embodiments said second member of said specific binding pair is a protein or peptide or nucleic acid. Such techniques can be implemented in accordance with known techniques for affinity purification, including but not limited to those described in U.S. Pat. Nos. 5,994,310; 5,834,318; 5,783,663; 5,726,293; and 5,364,531, or variations thereof that will be apparent to persons skilled in the art in view of the instant disclosure.

Catalysis. Another particular application of the invention is in a method of converting a first compound to a second compound by a catalytic reaction. In general such methods comprise providing an article of manufacture (including nanotube arrays and nanotube beds) as described herein, said article further comprising a secondary compound associated with said bilayer coating, wherein said secondary compound is a catalyst for said catalytic reaction; and then contacting a composition containing said first compound to said bilayer coating under conditions in which said first compound is catalytically converted to said second compound by said catalyst in said bilayer coating formed on said inner wall portion of said nanotube. In some embodiments the contacting step is carried out by continuously flowing said composition through said nanotube. In some embodiments the first compound is a protein or peptide; in some embodiments the catalyst is a protein or nucleic acid (such as an enzyme or ribozyme). Such techniques can be implemented in accordance with known techniques for biocatalysis, including but not limited to those described in U.S. Pat. Nos. 6,620,602; 6,613,552; 6,600,077; 6,472,190; 6,472,169; 5,583,267; and, with ribozymes, U.S. Pat. Nos. 6,716,973; 6,696,250; 6,605,429; 6,489,163; 6,482,803, or variations thereof that will be apparent to persons skilled in the art in view of the instant disclosure.

Biochips. Still other applications of the present invention provide a method of binding a target compound. In general such methods comprise providing an article of manufacture (including nanotube arrays and particularly patterned nanotube arrays) as described herein, contacting a composition containing said target compound to said array; and then detecting the binding of said target compound to a secondary compound in at least one of said separate and discrete regions of said array. The secondary compound may be proteins or peptides, or nucleic acid. The method may further comprise the step of identifying the secondary compound to which said secondary compound binds (e.g., by prior tagging of the compound, releasing and sequencing or analyzing the compound, or any other suitable technique). The method further comprises the step of identifying the test compound bound to said secondary compound (e.g., by releasing the compound and subjecting the compound to analytical techniques such as nuclear magnetic resonance, fluorescence, spectrophotometry, impedance analysis, etc.). Such techniques can be implemented in accordance with known techniques for making and using biochips, including but not limited to those described in U.S. Pat. Nos. 6,685,841; 6,673,544; 6,673,315; 6,671,625; 6,660,479; 6,649,342; 6,646,271; and 6,623,696, or variations thereof that will be apparent to persons skilled in the art in view of the instant disclosure.

Solution exchange. Nanotubes of the invention provide for convenient solution exchange (e.g., by replacing the solution or altering the composition of the solution). Thus another aspect of the invention is a method of altering the composition of a nanotube, comprising: (a) providing an article of manufacture as described herein (including nanotube beds and nanotube arrays), wherein said bilayer coating is hydrated with an aqueous solution along the entire length dimension of said nanotube; and then (b) introducing a solute into said aqueous solution along said entire length dimension of said nanotube. The solute may be a salt, buffer compound, small organic compound, or the like, or including combinations thereof, introduced to change a property of the solution such as buffering capacity, pH, salinity, etc. Typically the nanotube has an opening, said introducing step is carried out by contacting said solute to said opening, and said introducing step is preferably carried out within a time of ten minutes or even five minutes.

The present invention is explained in greater detail in the following non-limiting Examples.

EXAMPLES

Figure 2:
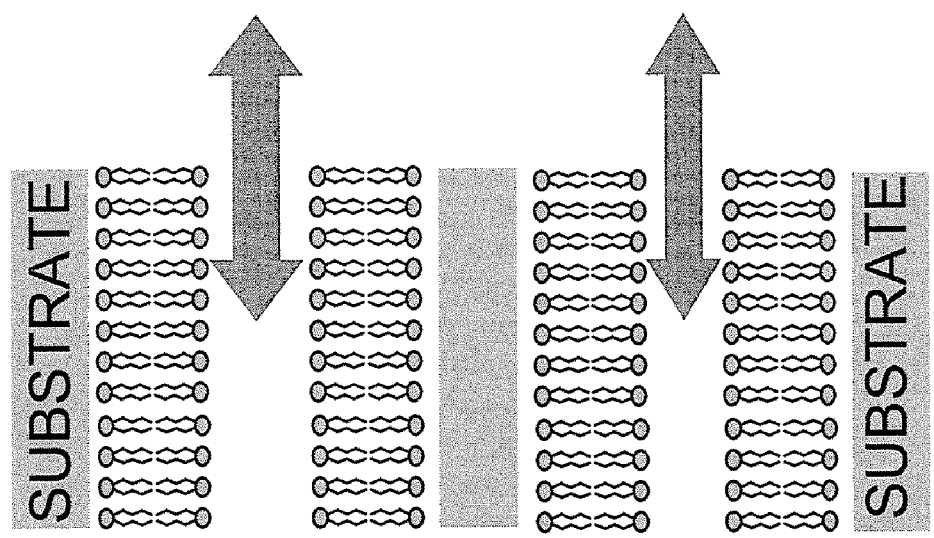
FIG. 2 illustrates a substrate-supported lipid nanotube array of the present invention.

As noted above, we here report on an alternative approach to building substrate-supported lipid bilayers by self-assembling cylindrical phospholipid structures inside the nanopores (see FIG. 2). Initial experiments we carried out with nanoporous anodic aluminum oxide (AAO) substrates because this well-studied material exhibits an aligned through-film porous structure that is suitable for designing vectorial transport assemblies.[8] The AAO pores are macroscopically homogeneous and hexagonally packed with the pore diameter tunable from ca. 4 to 200 nm.[9]

Figure 3:
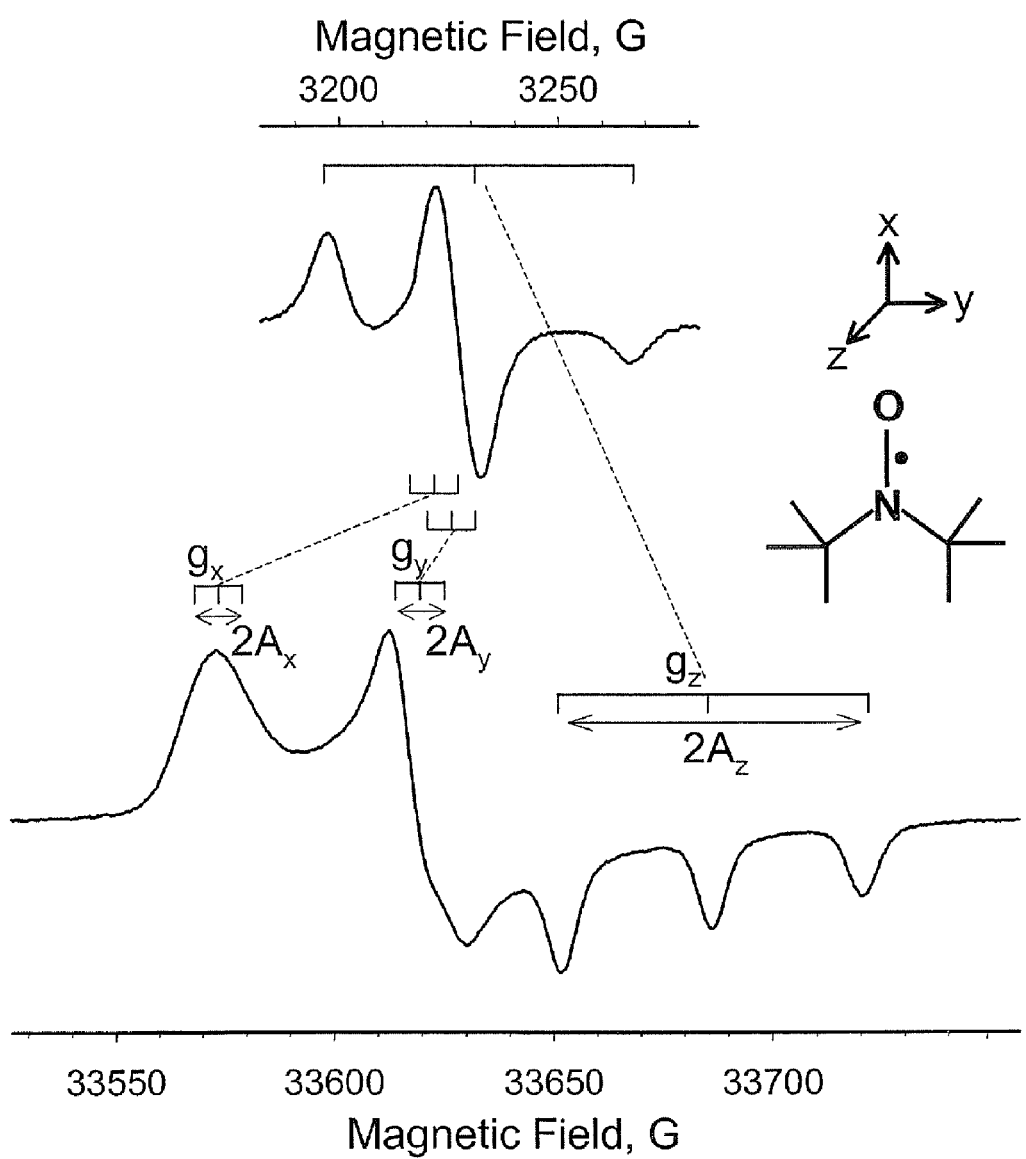
FIG. 3. Comparative rigid-limit (T=100 K) experimental EPR spectra of randomly dispersed DMPC: 5PC (100:1 molar ratio) bilayers at 9.0 GHz (top) and 94.4 GHz (bottom) and orientation of the nitroxide magnetic axes with respect to the molecular frame.

To characterize the structure of the phospholipids inside the nanopores, we have chosen spin-labeling EPR because this method is highly sensitive to the bilayer structure, can be used to study opaque and nontransparent materials, and causes minimal bilayer perturbation.[10] The method is based on labeling of a lipid molecule with a nitroxide, the spectrum of which reports on local dynamics, magnetic interactions, and molecular orientations.[10] This sensitivity of EPR to the orientation of a spin-bearing nitroxide moiety in the magnetic field is further enhanced at higher magnetic fields (>3 T, HF EPR) as illustrated in FIG. 3 with an example of rigid-limit spectra from spin-labeled bilayers. At these fields the nitroxide EPR spectra are dominated by g-factor anisotropy making the contributions from all three orientations of the principle axes in the magnetic field easily identifiable.

Figure 4:
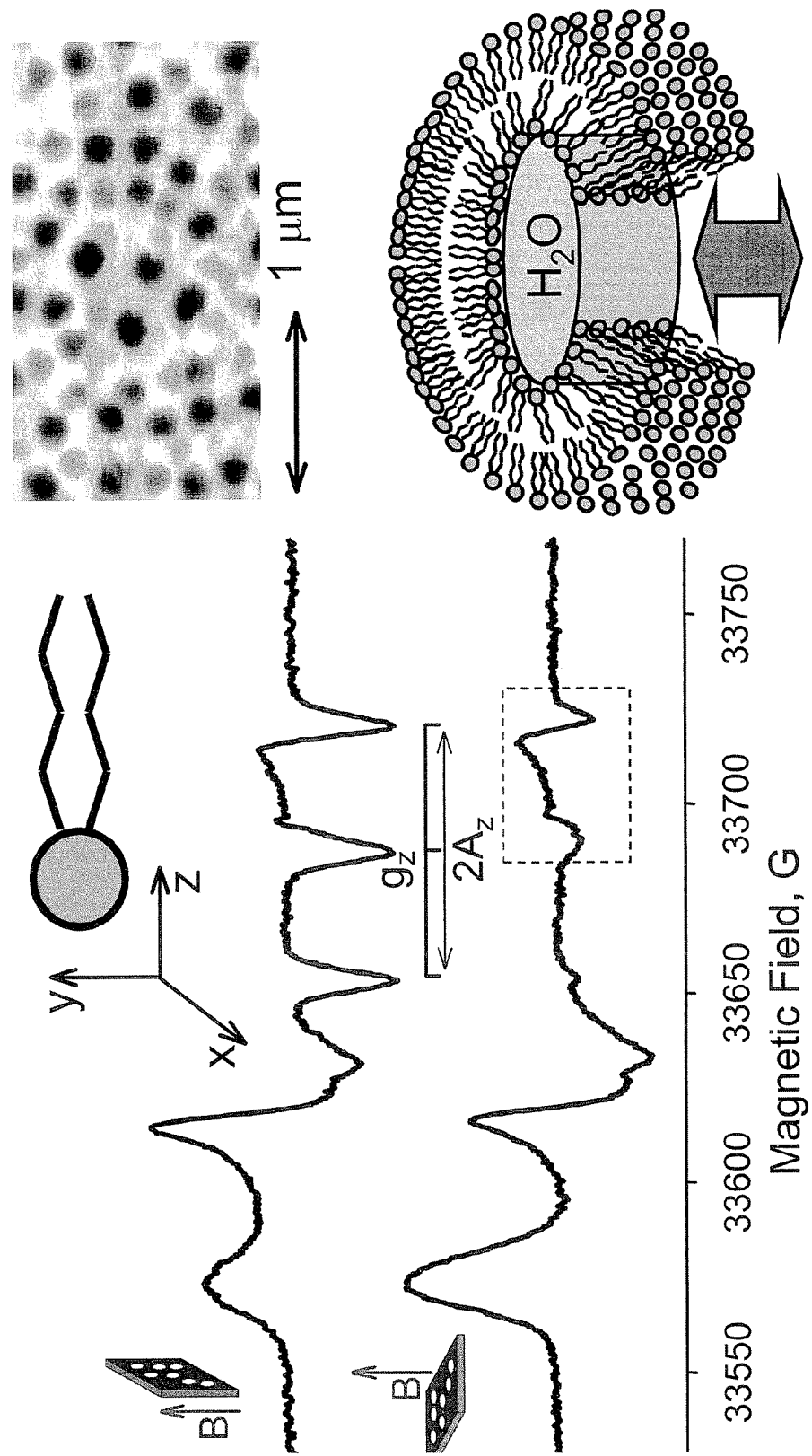
FIG. 4. Left: Experimental rigid limit (T=150 K) high resolution 94.4 GHz (W-band) EPR spectra of AAO substrate with deposited phospholipid DMPC:5PC (DMPC, 1,2-dimyristoyl-sn-glycero-3-phosphocholine; 5-PC, 1-palmitoyl-2-Stearoyl-(5-doxyl)-sn-glycero-3-phosphocholine) in 100:1 molar ratio at two orientations of the substrate surface in the magnetic field. A cartoon on the top shows orientations of the magnetic axes with respect to the phospholipid. Note that the bottom EPR spectrum has a low intensity in the $g_z$-region (the feature in the dashed box is due to a paramagnetic AAO impurity) indicating that at this substrate orientation the lipid chains are perpendicular to the magnetic field. Right: SEM (scanning electron microscopy) images of the substrate surface after heat treatment and a cartoon of a lipid nanotube fainted inside the substrate nanopores.

DMPC (1,2-dimyristoyl-sn-glycero-3-phosphocholine) was labeled with 1-palmitoyl-2-Stearoyl-(5-doxyl)-sn-glycero-3-phosphocholine (5PC, both from Avanti Polar Lipids, Alabaster, Ala.) in 100:1 molar ratio as described previously.[11] Clean AAO discs (Whatman Ltd., UK) were heated to ca. 650 K under <0.1 torr vacuum to eliminate strong background EPR signal(s) presumably due to defects in the alumina. This treatment did not affect the average AAO pore diameter of 100 nm verified by SEM (FIG. 4, top right). Lipids were deposited by exposing treated AAO discs from one side to a 20% phospholipid aqueous dispersion. After the deposition, an excess of lipid from the surface was carefully removed with Kimwipes EX-L. The samples, which were maintained fully hydrated, were characterized with conventional (X-band, 9.5 GHz) and high field (95 GHz) EPR spectroscopy at various orientations of the supporting AAO chip in the magnetic field.

The lipids in fluid bilayers undergo a complex anisotropic motion including fast rotations around the long axis, lateral diffusion, and flip-flop. The local dynamics of the lipid fatty acid chains is varied across the bilayer and can be characterized by the local order parameter S which is known to decrease progressively towards the center from ca. 0.7 at the C-5 position to 0.1-0.2 at C-16.[12] Thus, the lipid with a nitroxide label at the position 5, 5PC, would be more informative for studying alignment of the self-assembled lipid structures. Dynamic lipid disorder and partial averaging of spectral anisotropies can be further reduced by taking EPR spectra at low temperature so the dynamics of the phospholipids is approaching the rigid limit (150 K).

The largest changes in 5PC spectra upon reorientation of the AAO substrate in the magnetic field were observed at 95 GHz (W-band) because of an enhanced angular resolution of HF EPR over conventional X-band. The relative intensities of characteristic peaks of these spectra, FIG. 4 (left), are clearly different from those of randomly dispersed vesicles shown in FIG. 3 (bottom). These changes in the relative intensities are indicative of lipid alignment. Particularly noticeable are the changes in the $g_z$-region (i.e., high-field component which spreads from ca. 33850 to 33940 G): when the surface of the AAO substrate is perpendicular to the magnetic field (bottom spectrum), the z-component almost completely disappears (the signals inside the dashed box are mainly due to paramagnetic impurities in the AAO substrate). This means that at this substrate orientation only a very small fraction of molecules has the z-axis of the N—O frame aligned with the external magnetic field. The orientation of the nitroxide magnetic axes of 5PC is such that the z-axis is approximately aligned along the phospholipid chain (FIG. 3, cartoon in the right top corner). Thus, it must be concluded that a majority of the phospholipids inside the nanopores (since the surface phospholipids were mechanically removed during sample preparation) are positioned with their long axis perpendicular to the magnetic field and therefore perpendicular to the direction of pores. The AAO surface is known to be hydrophilic[13] and therefore in fully hydrated samples the lipids are organized in bilayers rather than in monolayers. The bilayer lipid organization was further confirmed by experiments with the lipids labeled at the end of the acyl chain (16PC; 1-palmitoyl-2-Stearoyl-(16-doxyl)-sn-glycero-3-phosphocholine): these samples produced EPR spectra essentially identical to those from unsupported liposomes (not shown). This is consistent with a lipid nanotube geometry shown in FIG. 3 (bottom right). The static order parameter of lipids in such a nanotube was determined by a "center of gravity" method[14] and was found to be exceptionally high $S_{static} \approx 0.9$.

Room temperature X- and W-band spectra of the AAO: DMPC: 5PC (not shown) were also found orientation-dependent but to a lesser degree. The latter indicated that the lipids inside the AAO nanopores remained mobile. Moreover, the local dynamic order parameters deduced from X-band EPR spectra were within 5% of those for aqueous DMPC liposomes. This indicates that the mobility of the lipids in the nanotubes we describe is very close to that of unsupported bilayers.

Overall, this example demonstrates that lipid bilayers can self-assemble into lipid nanotubes inside the nanoporous AAO substrate. We propose that substrate-supported lipid nanotube arrays have potential for building robust biochips and biosensors in which rigid nanoporous substrates protect the bilayer surface from contamination. The total bilayer surface in the lipid nanotube arrays is much greater than in the planar substrate-supported membranes. The lipid nanotube arrays seem to be suitable for developing patterned lipid deposition and could be potentially used for pattering of membrane-associated molecules.

Example 1

Sample preparation. DMPC (1,2-dimyristoyl-sn-glycero-3-phosphocholine), 5PC (1-palmitoyl-2-Stearoyl-(5-doxyl)-sn-glycero-3-phosphocholine), and 16-PC (1-palmitoyl-2-Stearoyl-(16-doxyl)-sn-glycero-3-phospho-choline) were purchased from Avanti Polar Lipids (Alabaster, Ala.) in form of chloroform solutions and were stored at 223 K in a freezer prior to use. Spin-labeled multilamellar liposomes were prepared by mixing chloroform solutions of DMPC and 5PC or 16PC (all at concentration of 10-20 mg lipid/ml) in 100:1 molar ratio. After the mixing chloroform was removed by a rotary evaporator yielding a thin lipid film on the sides of a round bottom flask. Residual chloroform was removed by keeping the vial on a vacuum pump with a nitrogen trap overnight. Multilamellar liposomes were formed by adding 50 mM TRIS pH=7.0 buffer and cycling the flask for at least five times between a container with liquid nitrogen and a water bath at 305 K. The final concentration of DPPC in aqueous media was 200 mg/ml.

Deposition of phospholipid bilayers onto AAO substrate was carried out by exposing one side of the AAO disk to the aqueous multilamellar liposomes at 303 K, which is above the DMPC main phase transition temperature. This exposure resulted in an immediate wetting of the nanoporous substrate, which became semitransparent. After ca. 5 min of exposure, excess of the phospholipids from both sides of the AAO chip was carefully removed by repetitive wiping of the surfaces with Kimwipes EX-L.

Alternatively, aqueous multilamellar liposomes were placed on one side of the AAO disc and pushed through the disk by either hydrostatic pressure of 1-10 bar or by centrifugation at greater than ten gravities. Excess of the phospholipids from both sides of the AAO chip was carefully removed as above.

Before EPR measurements the AAO/lipid sample was rehydrated by either immersing the entire AAO chip into aqueous buffer or maintaining the sample at 100% humidity for at least two hours.

EPR measurements. X-band (9 GHz) EPR measurements were carried out with a Varian (Palo Alto, Calif.) Century Series E-102 spectrometer. The W-band EPR spectrometer is described in Nilges, M. J.; Smirnov, A. I.; Clarkson, R. B.; Belford, R. L. *Appl. Magn. Reson.* 1999, 16, 167. The linearity of magnetic field scanning with a water-cooled coaxial sweep coil which has measured resettability of at least 30 mG and stability better than 10 ppm of the maximum scan width of 1100 G.

Magnetic field was calibrated after the measurements with a precision NMR teslameter PT 2025 (GMW Associates, Redwood City, Calif.). Magnetic field scans of the same width were used for both calibrations and experiments. To simplify the calibration procedure in experiments with nitroxide radicals, we have used 100 μM aqueous solution of perdeuterated Tempone (perdeuterated 2,2',6,6'-tetramethyl-4-piperidone-1-nitroxide or PDT, purchased from Cambridge Isotope Laboratories, Andover, Mass.) for cross-calibration of the magnetic field. The measurements of $A_{iso}$ from independently calibrated scans at X- and W-bands were found to be consistent and equal to 16.01±0.01 G while giso=2.00550 (6) was primarily determined from W-band measurement.

Figure 5A:
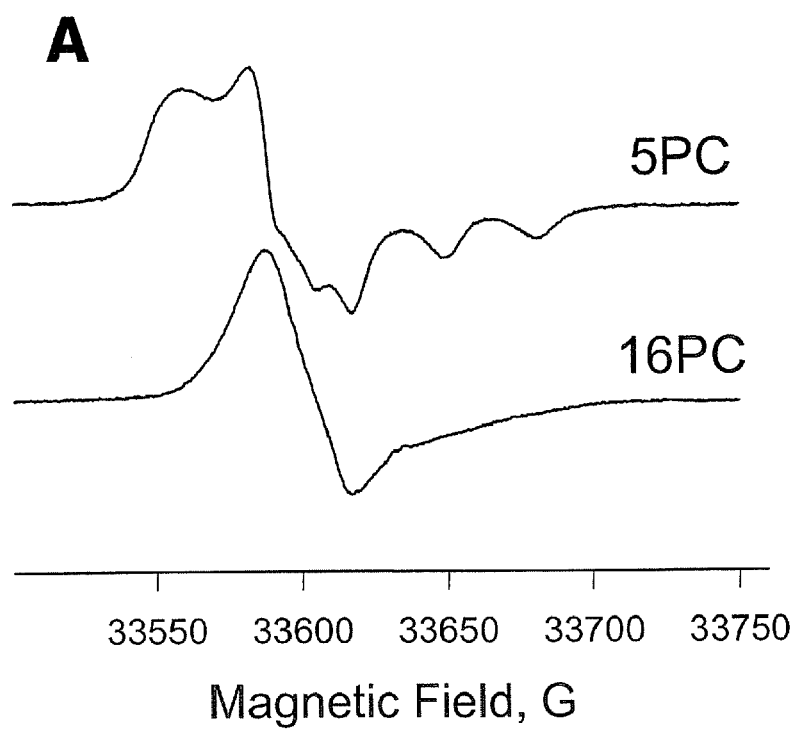
FIGS. 5A and 5B. Experimental room temperature (290 K) 94.4 GHz (W-band) EPR spectra if spin-labeled phospholipids. A—multilamellar unsupported DMPC liposomes (200 mg/ml) labeled with 5PC (i.e., at the position of the nitroxide reporter group close to the bilayer polar head region) and 16PC (16PC, 5-PC, 1-palmitoyl-2-Stearoyl-(16-doxyl)-sn-glycero-3-phosphocholine) close to the center of the bilayer). These spectra do not change with reorientation of the sample in the magnetic field. B—the same multilamellar DMPC liposomes after deposition onto nanoporous AAO substrate. These spectra were taken when the surface of the AAO substrate was perpendicular to the external magnetic field.
Figure 5B:
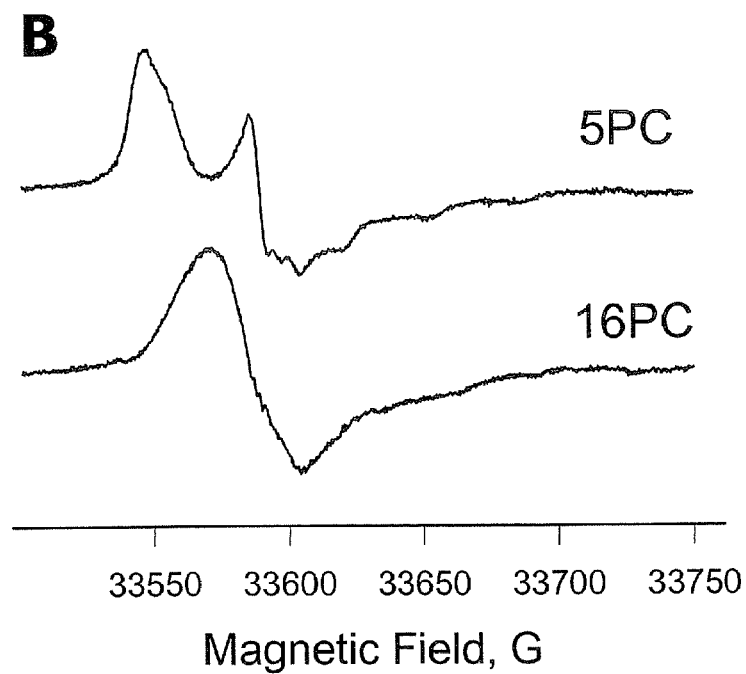

FIGS. 5A and 5B shows experimental room temperature (290 K) 94.4 GHz (W-band) EPR spectra pff spin-labeled phospholipids. A—multilamellar unsupported DMPC liposomes (200 mg/ml) labeled with 5PC (i.e., at the position close to the bilayer polar head region) and 16PC (close to the center of the bilayer). These spectra do not change with reorientation of the sample in the magnetic field. B—the same multilamellar DMPC liposomes after deposition onto nanoporous AAO substrate. These spectra were taken when the surface of the AAO substrate was perpendicular to the external magnetic field.

Note, that while the A and B spectra from 5PC are significantly different, the spectra from 16PC are practically the same. This means that rotational dynamics of 16PC which is located at the center of the bilayer is essentially the same for multilamellar unsupported liposomes and those deposited onto nanoporous AAO substrate. This also indicated that no monolayers are formed inside the nanopores: otherwise the dynamics of 16PC would be greatly restricted.

Example 2

Fast and Efficient Buffer Exchange with Nanopore-Supported Phospholipid Bilayers Because the nanoporous channels remain accessible to water-soluble molecules after the lipid bilayers are deposited, buffer and salt concentration can be easily adjusted in a very short time. Preliminary EPR and FRAP (Fluorescence Recovery After Photobleaching—not shown) experiments show that small solute molecules diffuse through nanoporous channels freely with characteristic times of a few seconds over the entire length of ca. 60 μm channels.

Figure 6:
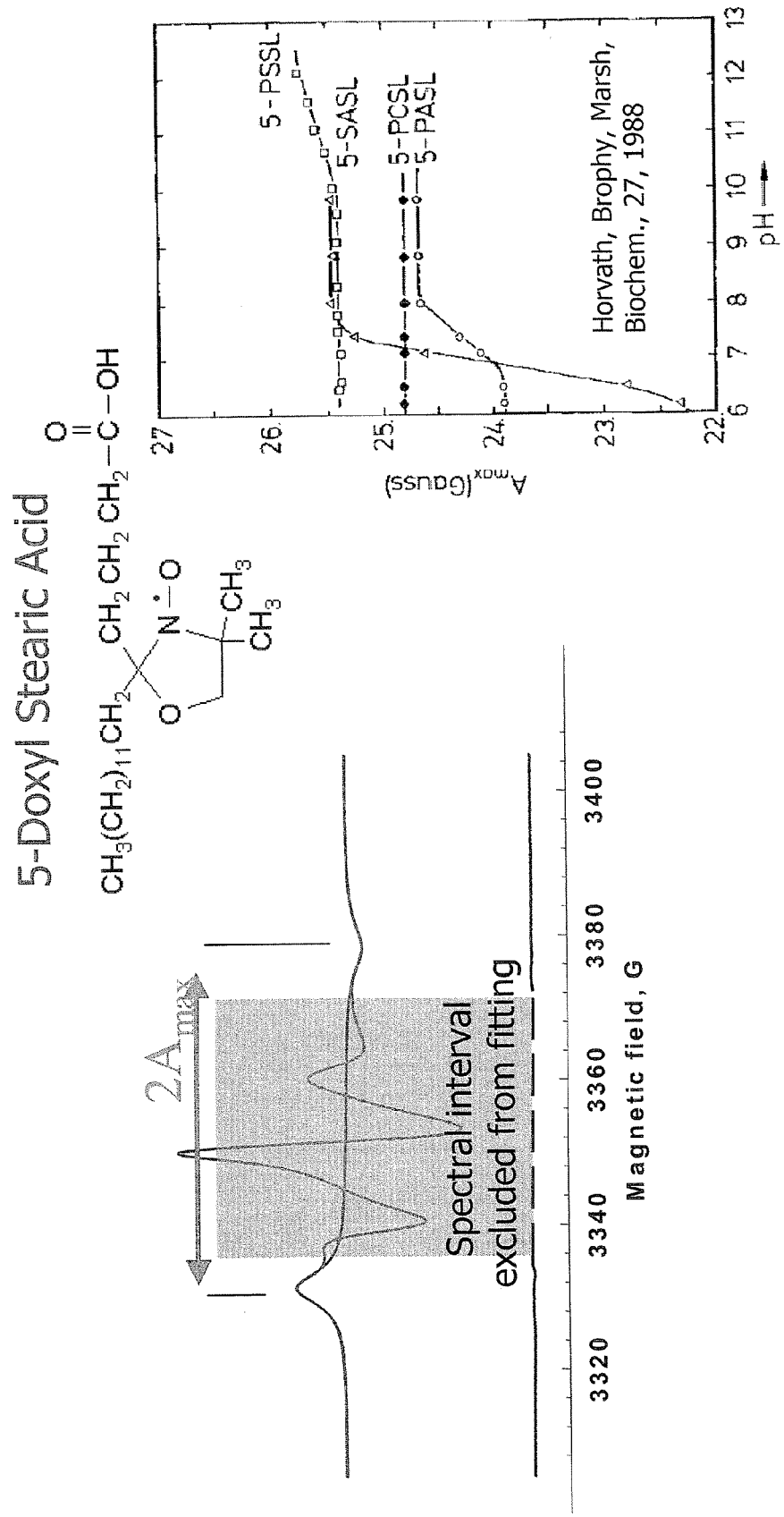
FIG. 6 illustrates the use of nanopore-supported bilayers for adjusting pH.
Figure 7:
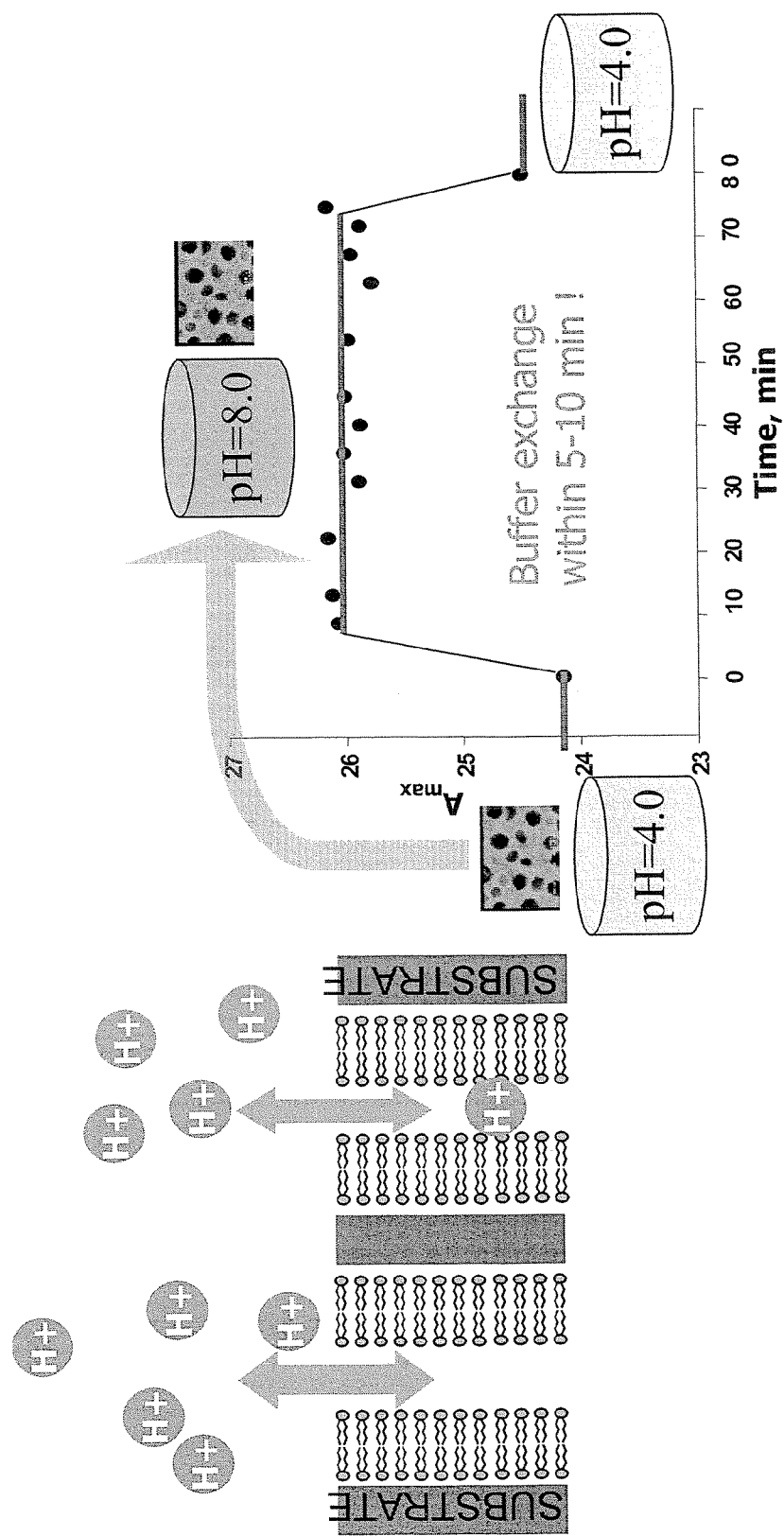
FIG. 7 illustrates the measurements of local pH for AAO-supported DMPC bilayer upon exchanging buffers from pH=4.0 to 8.0 and back to 4.0 units.
Figure 8:
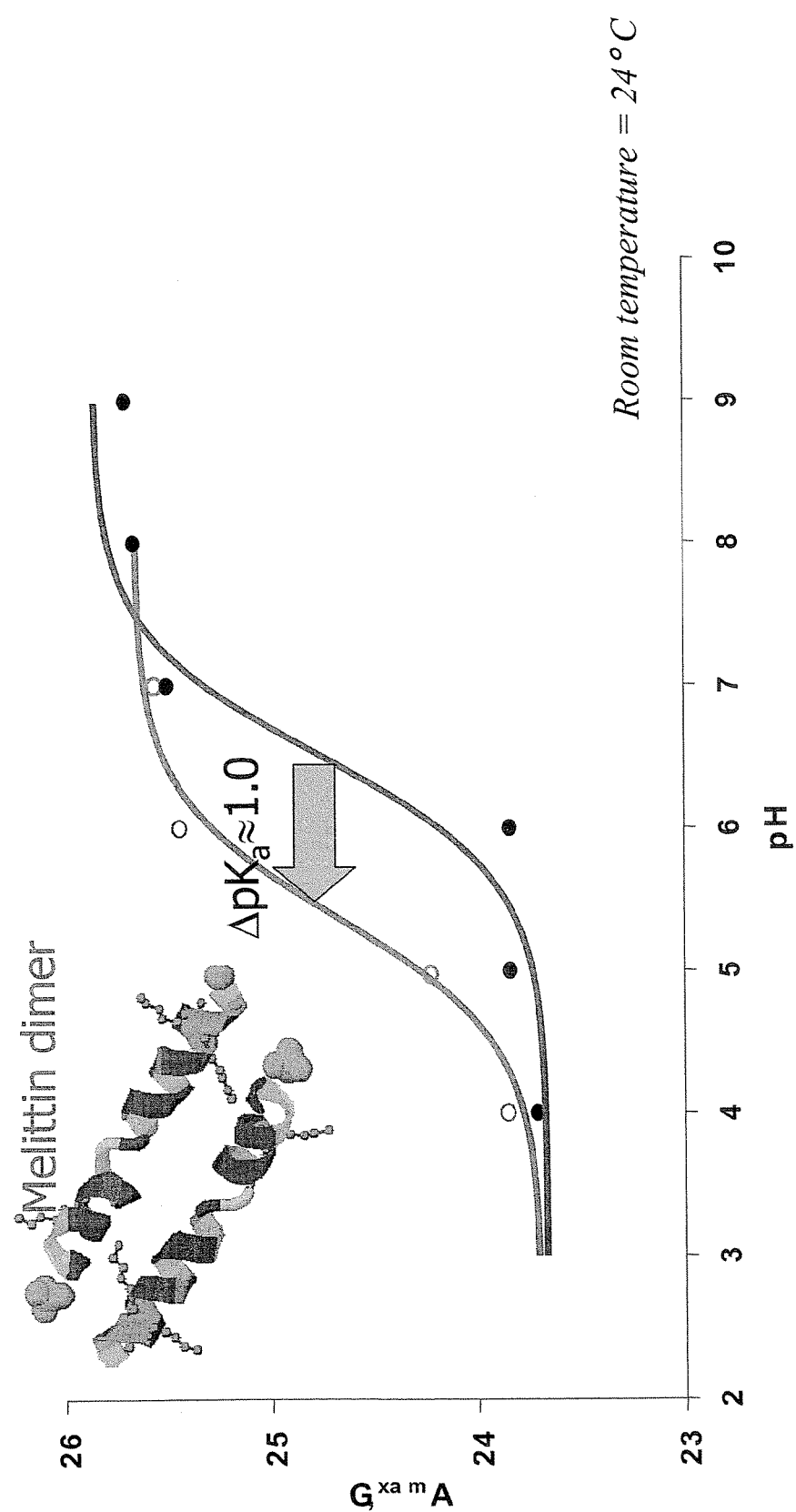
FIG. 8 illustrates the use of nanopore-supported phospholipids for measurements of local pK of the phospholipid bilayer in presence in absence of an alpha-helical peptide mellitin.

FIGS. 6-8 illustrates the use of nanopore-supported bilayers for adjusting pH. In this experiment local pH was monitored using a characteristic splitting of EPR spectra—parameter Amax—of 5-doxyl stearic acid (structure is shown in the FIG. 6—top), which was used to label phospholipid bilayer composed of DMPC (1,2-dimyristoyl-sn-glycero-3-phosphocholine) in 1:100 molar ratio. This method has been initially described by Marsch and coworkers in application to unsupported phospholipid bilayers and illustrated in FIG. 6.

FIG. 7 illustrates the measurements of local pH for AAO-supported DMPC bilayer upon exchanging buffers from pH=4.0 to 8.0 and back to 4.0 units. Initially, the EPR splitting was measured when the AAO substrate was bathed with a pH=4.0 standard buffer (VWR International, Bristol, Conn.). After the measurements, the substrate was quickly washed from the surface with distilled water, and then placed in a container containing a standard pH=8.0 buffer. Immediately after that a room temperature EPR spectrum was taken with a Varian (Palo Alto, Calif.) Century Series E-109 EPR Spectrometer. We estimate, that the pH=8.0 spectrum was taken in less than 5 min since the AAO lipid chip was bathed with this buffer. The EPR spectrum demonstrated that within this time the buffer has been already fully replaced. After monitoring the EPR splitting for an hour to ensure that no more changes were observed, the buffer replacement procedure was repeated this time from the buffer of pH=8.0 to that of pH=4.0. The EPR splitting returned to the initial value illustrating that the buffer exchange procedure is fully reversible.

FIG. 8 illustrates the use of nanopore-supported phospholipids for measurements of local pK of the phospholipid bilayer in presence in absence of an alpha-helical peptide mellitin (purchased from Sigma, St. Louis, Mo.) structure shown in the left of the FIG. 8). Binding of mellitin to the phospholipid bilayers causes a restriction of lipid acyl chain motion and affects local bilayer electrostatics (pK). The later is measured by monitoring the EPR splitting—parameter Amax—as a function of pH by replacing the buffers as described above. The titration curve for the control sample (DMPC with no mellitin bound) is shown in blue. After that, the AAO lipid chip was bathed in a 1 mM mellitin solution for 5 min. and the EPR titration experiment has been repeated. The resulting EPR titration curve is shown in Fig. C as green. It is clear, that the binding of mellitin decreased the local pK of DMPC bilayer by approximately 1 unit. The same result was observed for unsupported DMPC bilayer containing saturating amount of mellitin. While the shift in pK was identical in both experiments, the experiments carried out with the help of AAO-supported lipid nanotubes utilized the same membrane protein sample, while experiments with unsupported bilayers generally require multiple sample preparations or, alternatively, conventional buffer exchange procedures (such as dialysis, and, for example, re-suspension and consequent centrifugation).

This example demonstrates that this invention allows to exchange buffers quickly and easily by simply replacing the buffer in which the AAO lipid nanotube arrays are bathed. The buffer replacement procedure could be carried out multiple times so, for example, the entire titration curve could be obtained for the same sample. Similar procedures could be developed for testing binding of other small water soluble molecules of interest such as peptides and/or drugs. Thus, substrate-supported lipid nanotube arrays open an avenue for studying conformations of membrane proteins in phospholipid bilayers without the need of preparing multiple samples.

Example 3

Writing on Nanotube Arrays

Figure 9:
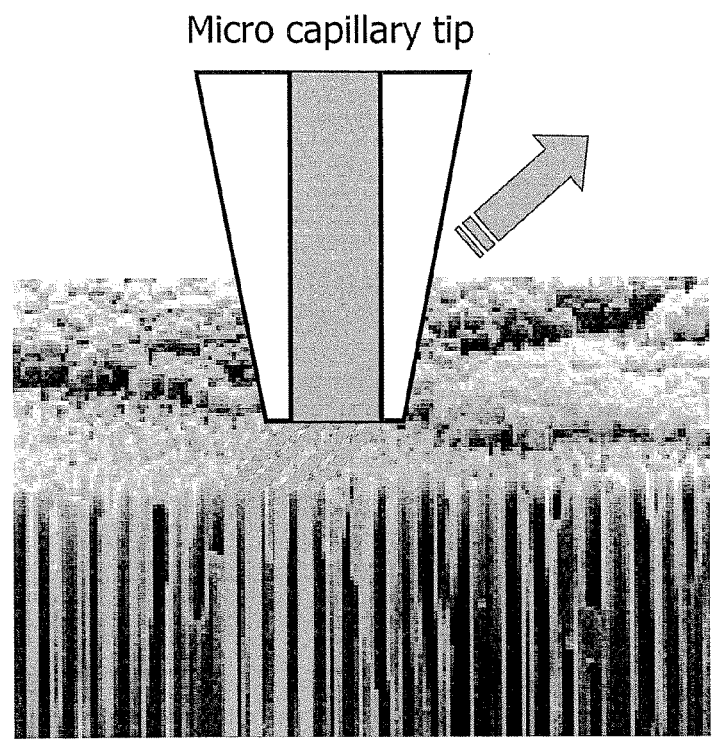
FIG. 9 illustrates microcapillary writing on the surface of the AAO substrate with the lipid transfer inside the lipid nanotubes.
Figure 10:
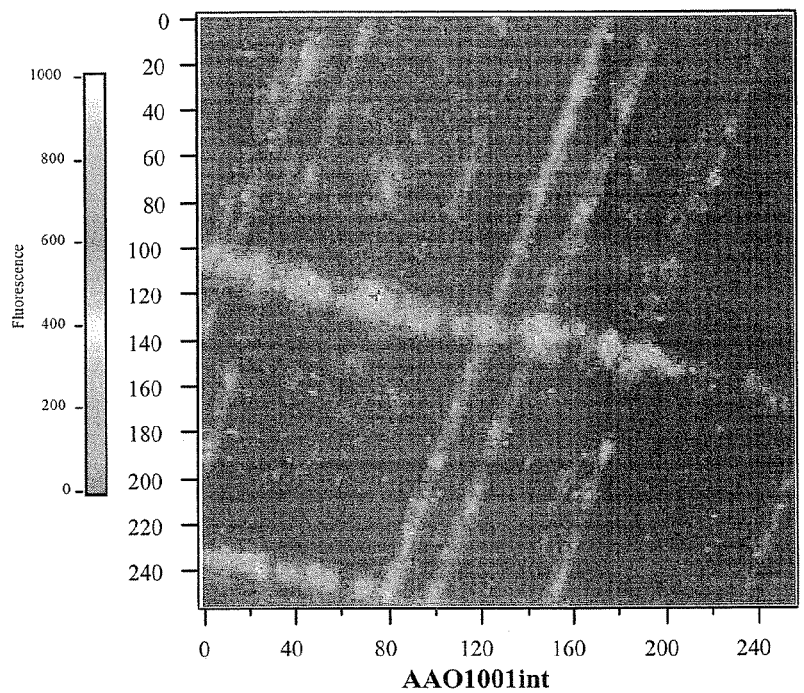
FIG. 10 illustrates preliminary results of "writing" on the surface of DMPC nanotube arrays with rhodamine-labeled phospholipid dispersion.

Phospholipid bilayers can be deposited onto nanoporous substrates using different techniques. FIGS. 9-10 demonstrate one such methods of depositing selectively labeled lipids (in this case—Phodamine-PE, 1,2-Dipalmitoyl-sn-Glycero-3-Phosphoethanolamine-N-(Lissamine Rhodamine B Sulfonyl); Ammonium Salt, purchased from Avanti Polar Lipids, Alabaster, Ala.) using a microcapillary tip that is controlled by a solenoid valve. In this example pattering was accomplished by transferring rhodamine-labeled bilayer dispersions from a fine tip and moving that tip over the AAO surface. Excess of phospholipids from the surface was removed by a 5 min low power sonication of the AAO chip bathed in an excess of buffer at 30° C. After that, the sample was kept in a buffer for 3 days at 4° C. and then fluorescence images were taken with a two-photon microscope. A sample image from such an experiment (FIG. 10) shows a clear pattern of perpendicular lines.

Another possible direction for creating distinctive patterns in lipid nanotube arrays would be a modification of a polymer lift-off technique which was recently developed for creating patches of fluid lipid bilayer on planar surfaces. In the original method the silicone surface is masked by a weakly attached polymer film. The film is made out of di-para-xylylene (Parylene C) or other suitable material which may be vapor deposited on a substrate such as a silicon substrate and then patterned using conventional techniques such photolithography. At the end of the process the chip is submerged in water and the film is easily removed. Depending on whether such a mask remains mainly intact after the lift-off, it might be possible to re-use it to mask the entrances to the AAO nanopores.

REFERENCES (1) H. McConnell et al., *Proc. Natl. Acad. Sci. U.S.A.* 1984, 81, 3249-3253.
(2) A. Brian et al., *Proc. Natl. Acad. Sci. U.S.A.* 1984, 81, 6159-6163.
(3) (a) E. Sackmann, *Science,* 1996, 271, 43-48; (b) S. Boxer et al., *J. Phys. Chem. B,* 1999, 103, 2554-2559; (c) C. Keller et al., *Phys. Rev. Lett.,* 2000, 84, 5443-5446.
(4) (a) S. Boxer, *Curr. Opinion Chem. Biol.,* 2000, 4, 704-709; (b) J. Groves et al., *Acc. Chem. Res.,* 2002, 35, 149-157.
(5) (a) J. Groves et al., *Science,* 1997, 275, 651-653; (b) L. Kam, *J. Am. Chem. Soc.,* 2000, 122, 12900-12902; (c) J. Hovis et al., *Langmuir,* 2001, 17, 3400-3405.
(6) C. Hennesthal et al., *J. Am. Chem. Soc.,* 2000, 122, 8085-8086.
(7) (a) Y. Dufrêne et al., *Biochim. Biophys. Acta,* 2000, 1509, 14-41; (b) D. Marchal et al., *Langmuir,* 2001, 17, 8313-8320.
(8) C. Martin, *Chem. Mater.,* 1996, 8, 1739-1746.
(9) (a) R. Furneaux et al., *Nature,* 1989, 337, 147-149; (b) D. Routkevitch et al., *Chem. Phys.,* 1996, 210, 343-352; (c) D. Routkevitch et al., *J. Phys. Chem.,* 1996, 100, 14037-14047.
(10) *Spin Labeling. Theory and Applications*; Berliner, L. J. Ed.; Academic Press; New York, 1976, 592 p.
(11) A. Smirnov et al., *Appl. Magn. Reson.,* 2001, 21, 453-467.
(12) O. Griffith et al., in *Spin Labeling. Theory and Applications*; Berliner, L. J. Ed.; Academic Press; New York, 1976, 453-560.
(13) M. Liew et al., *Biotechnol. Bioeng.,* 1997, 56, 89-98.
(14) O. Grinberg et al., *Soy. J. Chem. Phys.,* 1990, 6, 2685-2704.

The foregoing is illustrative of the present invention, and is not to be construed as limiting thereof. The invention is defined by the following claims, with equivalents of the claims to be included therein.

That which is claimed is:

1. A method of binding a first member of a specific binding pair, comprising:
providing an article of manufacture comprising:
(a) a nanotube having an inner wall portion, said nanotube having (i) an inner diameter between 10 nanometers and 500 nanometers and (ii) a length from two to one thousand times said diameter; and
(b) a bilayer coating formed on and parallel to said inner wall portion, such that only the hydrophilic portion of the bilayer coating is in contact with said inner wall portion, with said bilayer coating comprised of (i) from 10 to 90 percent by weight surfactants and (ii) from 10 to 90 percent by weight water,
said article further comprising a secondary compound associated with said bilayer coating, wherein said secondary compound is a second member of said specific binding pair; and then contacting a composition containing said first member of said specific binding pair to said article of manufacture so that first member of said specific binding pair binds to said second member of said specific binding pair and is thereby bound to bilayer coating formed on said inner wall portion of said nanotube.

2. The method of claim 1, further comprising the steps of:
separating said composition from said article of manufacture; and then
releasing said first member of said specific binding pair from said second member of said specific binding pair.

3. The method of claim 1, wherein said first member of said specific binding pair is a protein, peptide, or nucleic acid.

4. The method of claim 1, wherein said first member of said specific binding pair is a protein, peptide or nucleic acid.

5. A method of converting a first compound to a second compound by a catalytic reaction, comprising:
providing an article of manufacture comprising:
(a) a nanotube having an inner wall portion, said nanotube having (i) an inner diameter between 10 nanometers and 500 nanometers and (ii) a length from two to one thousand times said diameter; and
(b) a bilayer coating formed on and parallel to said inner wall portion, such that only the hydrophilic portion of the bilayer coating is in contact with said inner wall portion, with said bilayer coating comprised of (i) from 10 to 90 percent by weight surfactants and (ii) from 10 to 90 percent by weight water,
said article further comprising a secondary compound associated with said bilayer coating, wherein said secondary compound is a catalyst for said catalytic reaction; and then
contacting a composition containing said first compound to said bilayer coating under conditions in which said first compound is catalytically converted to said second compound by said catalyst in said bilayer coating formed on said inner wall portion of said nanotube.

6. The method of claim 5, wherein said contacting step is carried out by continuously flowing said composition through said nanotube.

7. The method of claim 5, wherein said first compound is a protein or peptide.

8. The method of claim 5, wherein said catalyst is a protein or nucleic acid.

9. A method of binding a target compound, comprising:
providing a patterned nanotube array comprising:
(a) a substrate having a plurality of nanotubes formed therein, each of said nanotubes having (i) an inner wall portion (ii) an inner diameter between 10 nanometers and 500 nanometers and (iii) a length from two to one thousand times said diameter; and
(b) a bilayer coating formed on and parallel to each of said inner wall portions, such that only the hydrophilic portion of the bilayer coating is in contact with said inner wall portions, with said bilayer coating comprised of (i) from 10 to 90 percent by weight surfactants and (ii) from 10 to 90 percent by weight water; and (c) a secondary compound associated with said bilayer coating, wherein said secondary compound in each one of said separate and discrete regions differs from said secondary compound in each of the other separate and discrete regions;

contacting a composition containing said target compound to said array; and then detecting the binding of said target compound to said secondary compound in at least one of said separate and discrete regions.

10. The method of claim 9, wherein said secondary compounds comprise proteins or peptides.

11. The method of claim 9, wherein said secondary compounds comprise nucleic acids.

12. The method of claim 9, further comprising the step of identifying the secondary compound to which said secondary compound binds.

13. The method of claim 9, further comprising the step of identifying the test compound bound to said secondary compound.

14. A method of altering the composition of a nanotube, comprising:

(A) providing an article of manufacture comprising:

(a) a nanotube having an inner wall portion, said nanotube having (i) an inner diameter between 10 nanometers and 500 nanometers and (ii) a length from two to one thousand times said diameter; and (b) a bilayer coating formed on and parallel to said inner wall portion, such that only the hydrophilic portion of the bilayer coating is in contact with said inner wall portion, with said bilayer coating comprised of (i) from 10 to 90 percent by weight surfactants and (ii) from 10 to 90 percent by weight water, wherein said bilayer coating is hydrated with an aqueous solution along the entire length dimension of said nanotube; and then (B) introducing a solute into said aqueous solution along said entire length dimension of said nanotube.

15. The method of claim 14, wherein said nanotube has an opening, said introducing step is carried out by contacting said solute to said opening, and said introducing step is carried out within a time of ten minutes.

* * * * *